(12) United States Patent
Voltenburg, Jr. et al.

(10) Patent No.: US 8,083,503 B2
(45) Date of Patent: Dec. 27, 2011

(54) PERISTALTIC PUMP ASSEMBLY AND REGULATOR THEREFOR

(75) Inventors: Robert R. Voltenburg, Jr., Davison, MI (US); Loren M. Thompson, Lapeer, MI (US)

(73) Assignee: Curlin Medical Inc., East Aurora, NY (US)

( * ) Notice: Subject to any disclaimer, the term of this patent is extended or adjusted under 35 U.S.C. 154(b) by 1033 days.

(21) Appl. No.: 11/862,326

(22) Filed: Sep. 27, 2007

(65) Prior Publication Data

US 2009/0087325 A1   Apr. 2, 2009

(51) Int. Cl.
*F04B 43/12* (2006.01)
(52) U.S. Cl. .................. 417/477.11; 417/477.2
(58) Field of Classification Search ............ 417/477.11, 417/477.9, 477.12, 477.2; 694/153
See application file for complete search history.

(56) References Cited

U.S. PATENT DOCUMENTS

| | | | |
|---|---|---|---|
| 3,675,653 A * | 7/1972 | Crowley et al. | 604/120 |
| 3,723,030 A * | 3/1973 | Gelfand | 417/475 |
| 3,876,340 A * | 4/1975 | Thomas | 417/475 |
| 3,921,622 A | 11/1975 | Cole | |
| 3,963,023 A | 6/1976 | Hankinson | |
| 4,178,138 A | 12/1979 | Iles | |
| 4,187,057 A | 2/1980 | Xanthopoulos | |
| 4,256,437 A | 3/1981 | Brown | |
| 4,418,565 A | 12/1983 | St. John | |
| 4,460,358 A | 7/1984 | Somerville et al. | |
| 4,537,561 A | 8/1985 | Xanthopoulos | |
| 4,544,336 A * | 10/1985 | Faeser et al. | 417/412 |
| 4,565,500 A | 1/1986 | Jeensalute et al. | |
| 4,599,055 A | 7/1986 | Dykstra | |
| 4,673,334 A | 6/1987 | Allington et al. | |
| 4,722,224 A | 2/1988 | Scheller et al. | |
| 4,735,558 A | 4/1988 | Kienholz et al. | |
| 4,764,116 A | 8/1988 | Shoher et al. | |
| 4,798,580 A | 1/1989 | DeMeo et al. | |
| 4,821,558 A | 4/1989 | Pastrone et al. | |
| 4,846,792 A | 7/1989 | Bobo, Jr. et al. | |
| 4,863,425 A | 9/1989 | Slate et al. | |
| 4,865,584 A | 9/1989 | Epstein et al. | |

(Continued)

FOREIGN PATENT DOCUMENTS

CA   2479707   3/2005

(Continued)

OTHER PUBLICATIONS

The International Bureau of WIPO, International Preliminary Report on Patentability in International Application No. PCT/US20081011131, issued Mar. 30, 2010.

(Continued)

*Primary Examiner* — Devon C Kramer
*Assistant Examiner* — Dnyanesh Kasture
(74) *Attorney, Agent, or Firm* — Hodgson Russ LLP

(57) ABSTRACT

A peristaltic pump assembly includes a pump body and a cassette removably attached thereto, wherein the cassette includes a race configured to provide a compression surface for a tube supported by the cassette. A roller assembly is operatively connected to the pump body, wherein the roller assembly includes a plurality of rollers configured to apply a predetermined force to the tube, thereby compressing the tube against the race. The peristaltic pump assembly further includes a regulator disposed in the pump body and operatively connected to the cassette, where the regulator is configured to regulate the predetermined force applied to the tube.

13 Claims, 2 Drawing Sheets

U.S. PATENT DOCUMENTS

| | | |
|---|---|---|
| 4,884,013 A | 11/1989 | Jackson et al. |
| 4,886,431 A | 12/1989 | Soderquist et al. |
| 4,909,713 A | 3/1990 | Finsterwald et al. |
| 4,943,279 A | 7/1990 | Samiotes et al. |
| 4,944,191 A | 7/1990 | Pastrone et al. |
| 4,950,235 A | 8/1990 | Slate et al. |
| 4,950,245 A | 8/1990 | Brown et al. |
| 4,978,335 A | 12/1990 | Arthur, III |
| 4,979,940 A | 12/1990 | Bobo, Jr. et al. |
| 4,981,467 A | 1/1991 | Bobo, Jr. et al. |
| 5,000,663 A | 3/1991 | Gorton |
| 5,006,110 A | 4/1991 | Garrison et al. |
| 5,011,378 A | 4/1991 | Brown et al. |
| 5,041,086 A | 8/1991 | Koenig et al. |
| 5,053,747 A | 10/1991 | Slate et al. |
| 5,059,171 A | 10/1991 | Bridge et al. |
| 5,064,412 A | 11/1991 | Henke et al. |
| 5,078,683 A | 1/1992 | Sancoff et al. |
| 5,096,385 A | 3/1992 | Georgi et al. |
| 5,098,380 A | 3/1992 | Aizawa et al. |
| 5,102,392 A | 4/1992 | Sakai et al. |
| 5,106,366 A | 4/1992 | Steppe |
| 5,116,203 A | 5/1992 | Natwick et al. |
| 5,125,891 A | 6/1992 | Hossain et al. |
| 5,126,616 A | 6/1992 | Gorton et al. |
| 5,163,900 A | 11/1992 | Wortrich |
| 5,176,631 A | 1/1993 | Koenig |
| 5,177,993 A | 1/1993 | Beckman et al. |
| 5,181,910 A | 1/1993 | Scanlon |
| 5,191,795 A | 3/1993 | Fellingham et al. |
| 5,195,960 A | 3/1993 | Hossain et al. |
| 5,213,483 A | 5/1993 | Flaherty et al. |
| 5,219,330 A | 6/1993 | Bollish et al. |
| 5,242,408 A | 9/1993 | Jhuboo et al. |
| 5,256,156 A | 10/1993 | Kern et al. |
| 5,256,157 A | 10/1993 | Samiotes et al. |
| 5,267,956 A | 12/1993 | Beuchat |
| 5,282,787 A | 2/1994 | Wortrich |
| 5,292,306 A | 3/1994 | Wynkoop et al. |
| 5,317,506 A | 5/1994 | Coutre et al. |
| 5,328,460 A | 7/1994 | Lord et al. |
| 5,337,747 A | 8/1994 | Neftel |
| 5,338,157 A | 8/1994 | Blomquist |
| 5,356,378 A | 10/1994 | Doan |
| 5,380,173 A | 1/1995 | Hellstrom |
| 5,387,088 A | 2/1995 | Knapp et al. |
| 5,394,732 A | 3/1995 | Johnson et al. |
| 5,395,320 A | 3/1995 | Padda et al. |
| 5,397,222 A | 3/1995 | Moss et al. |
| 5,427,509 A | 6/1995 | Chapman et al. |
| 5,429,602 A | 7/1995 | Hauser |
| 5,433,588 A | 7/1995 | Monk et al. |
| 5,445,506 A | 8/1995 | Afflerbaugh et al. |
| 5,447,417 A | 9/1995 | Kuhl et al. |
| 5,462,416 A | 10/1995 | Dennehey et al. |
| 5,480,294 A | 1/1996 | Di Perna et al. |
| 5,480,386 A | 1/1996 | Brohy et al. |
| 5,482,438 A | 1/1996 | Anderson et al. |
| 5,482,446 A | 1/1996 | Williamson et al. |
| 5,485,408 A | 1/1996 | Blomquist |
| 5,501,665 A | 3/1996 | Jhuboo et al. |
| 5,514,102 A | 5/1996 | Winterer et al. |
| 5,515,713 A | 5/1996 | Saugues et al. |
| 5,518,378 A | 5/1996 | Neftel et al. |
| 5,537,853 A | 7/1996 | Finburgh et al. |
| 5,538,405 A | 7/1996 | Patno et al. |
| D376,848 S | 12/1996 | Zeilig et al. |
| 5,588,815 A | 12/1996 | Zaleski, II |
| 5,601,420 A | 2/1997 | Warner et al. |
| 5,609,575 A | 3/1997 | Larson et al. |
| 5,620,312 A | 4/1997 | Hyman et al. |
| 5,626,563 A | 5/1997 | Dodge et al. |
| 5,628,619 A | 5/1997 | Wilson |
| D380,260 S | 6/1997 | Hyman |
| 5,637,093 A | 6/1997 | Hyman et al. |
| 5,646,727 A | 7/1997 | Hammer et al. |
| 5,647,853 A | 7/1997 | Feldmann et al. |
| 5,655,897 A | 8/1997 | Neftel et al. |
| 5,657,000 A | 8/1997 | Ellingboe |
| 5,658,250 A | 8/1997 | Blomquist et al. |
| 5,669,877 A | 9/1997 | Blomquist |
| 5,676,530 A | 10/1997 | Nazarifar |
| 5,680,111 A | 10/1997 | Danby et al. |
| 5,681,285 A | 10/1997 | Ford et al. |
| 5,683,367 A | 11/1997 | Jordan et al. |
| 5,685,844 A | 11/1997 | Marttila |
| 5,695,473 A | 12/1997 | Olsen |
| 5,709,539 A | 1/1998 | Hammer et al. |
| 5,713,856 A | 2/1998 | Eggers et al. |
| 5,718,568 A | 2/1998 | Neftel et al. |
| 5,720,721 A | 2/1998 | Dumas et al. |
| 5,741,125 A | 4/1998 | Neftel et al. |
| 5,752,813 A | 5/1998 | Tyner et al. |
| 5,755,691 A | 5/1998 | Hilborne |
| 5,759,015 A | 6/1998 | Van Lintel et al. |
| 5,764,159 A | 6/1998 | Neftel |
| 5,766,155 A | 6/1998 | Hyman et al. |
| 5,772,635 A | 6/1998 | Dastur et al. |
| 5,782,611 A | 7/1998 | Neftel et al. |
| 5,782,805 A | 7/1998 | Meinzer et al. |
| 5,788,669 A | 8/1998 | Peterson |
| 5,791,880 A | 8/1998 | Wilson |
| 5,795,317 A | 8/1998 | Brierton et al. |
| 5,795,327 A | 8/1998 | Wilson et al. |
| 5,800,387 A | 9/1998 | Duffy et al. |
| 5,811,659 A | 9/1998 | Giebler |
| 5,827,223 A | 10/1998 | Butterfield |
| 5,827,262 A | 10/1998 | Neftel et al. |
| 5,836,910 A | 11/1998 | Duffy et al. |
| 5,840,068 A | 11/1998 | Cartledge et al. |
| 5,842,841 A | 12/1998 | Danby et al. |
| 5,843,035 A | 12/1998 | Bowman et al. |
| 5,848,988 A | 12/1998 | Davis |
| 5,853,386 A | 12/1998 | Davis et al. |
| 5,897,524 A | 4/1999 | Wortrich et al. |
| 5,904,668 A | 5/1999 | Hyman et al. |
| 5,906,589 A | 5/1999 | Gordon et al. |
| 5,927,956 A | 7/1999 | Lim et al. |
| 5,928,196 A | 7/1999 | Johnson et al. |
| 5,935,099 A | 8/1999 | Peterson et al. |
| 5,935,106 A | 8/1999 | Olsen |
| 5,938,413 A | 8/1999 | Makino et al. |
| 5,941,846 A | 8/1999 | Duffy et al. |
| 5,954,485 A | 9/1999 | Johnson et al. |
| 5,961,487 A | 10/1999 | Davis |
| 5,968,014 A | 10/1999 | Neftel et al. |
| 5,984,894 A | 11/1999 | Poulsen et al. |
| 5,989,222 A | 11/1999 | Cole et al. |
| 5,993,420 A | 11/1999 | Hyman et al. |
| 6,013,057 A | 1/2000 | Danby et al. |
| 6,059,765 A | 5/2000 | Cole et al. |
| 6,068,612 A | 5/2000 | Bowman et al. |
| 6,077,055 A | 6/2000 | Vilks |
| 6,077,246 A | 6/2000 | Kullas et al. |
| 6,085,574 A | 7/2000 | Neftel et al. |
| 6,106,498 A | 8/2000 | Friedli et al. |
| 6,109,895 A | 8/2000 | Ray et al. |
| 6,110,153 A | 8/2000 | Davis et al. |
| 6,120,490 A | 9/2000 | Neftel |
| 6,123,524 A | 9/2000 | Danby et al. |
| 6,129,517 A | 10/2000 | Danby et al. |
| 6,129,699 A | 10/2000 | Haight et al. |
| 6,142,008 A | 11/2000 | Cole et al. |
| 6,146,109 A | 11/2000 | Davis et al. |
| 6,195,887 B1 | 3/2001 | Danby et al. |
| 6,203,296 B1 | 3/2001 | Ray et al. |
| 6,203,528 B1 | 3/2001 | Deckert et al. |
| 6,212,936 B1 | 4/2001 | Meisberger |
| 6,213,723 B1 | 4/2001 | Danby et al. |
| 6,213,738 B1 | 4/2001 | Danby et al. |
| 6,231,320 B1 | 5/2001 | Lawless et al. |
| 6,234,992 B1 | 5/2001 | Haight et al. |
| 6,241,704 B1 | 6/2001 | Peterson et al. |
| 6,248,067 B1 | 6/2001 | Causey, III et al. |
| 6,261,262 B1 | 7/2001 | Briggs et al. |
| 6,269,340 B1 | 7/2001 | Ford et al. |
| D446,854 S | 8/2001 | Cheney, II et al. |

| | | | | | |
|---|---|---|---|---|---|
| 6,270,673 B1 | 8/2001 | Belt et al. | 2002/0193679 A1 | 12/2002 | Malave et al. |
| 6,280,430 B1 | 8/2001 | Neftel et al. | 2003/0004458 A1 | 1/2003 | Platt et al. |
| 6,293,926 B1 | 9/2001 | Sorensen et al. | 2003/0060765 A1 | 3/2003 | Campbell et al. |
| 6,328,712 B1 | 12/2001 | Cartledge et al. | 2003/0106553 A1 | 6/2003 | Vanderveen |
| 6,358,225 B1 | 3/2002 | Butterfield | 2003/0139701 A1 | 7/2003 | White et al. |
| 6,362,591 B1 | 3/2002 | Moberg | 2003/0140928 A1 | 7/2003 | Bui et al. |
| 6,364,279 B1 | 4/2002 | Neftel et al. | 2003/0140929 A1 | 7/2003 | Wilkes et al. |
| 6,419,466 B1 * | 7/2002 | Lowe et al. ............. 417/477.11 | 2003/0141368 A1 | 7/2003 | Pascual et al. |
| 6,423,029 B1 | 7/2002 | Elsberry | 2003/0141981 A1 | 7/2003 | Bui et al. |
| 6,447,481 B1 | 9/2002 | Duchon et al. | 2003/0144878 A1 | 7/2003 | Wilkes et al. |
| 6,468,059 B2 | 10/2002 | Haser et al. | 2003/0144881 A1 | 7/2003 | Talachian et al. |
| 6,475,180 B2 | 11/2002 | Peterson et al. | 2003/0144882 A1 | 7/2003 | Talachian et al. |
| 6,489,896 B1 | 12/2002 | Platt et al. | 2003/0201697 A1 | 10/2003 | Richardson |
| 6,519,569 B1 | 2/2003 | White et al. | 2003/0204414 A1 | 10/2003 | Wilkes et al. |
| 6,539,250 B1 | 3/2003 | Bettinger | 2003/0204416 A1 | 10/2003 | Radpay et al. |
| 6,551,276 B1 | 4/2003 | Mann et al. | 2003/0204419 A1 | 10/2003 | Wilkes et al. |
| 6,554,791 B1 | 4/2003 | Cartledge et al. | 2003/0204420 A1 | 10/2003 | Wilkes et al. |
| 6,554,798 B1 | 4/2003 | Mann et al. | 2003/0212364 A1 | 11/2003 | Mann et al. |
| 6,555,986 B2 | 4/2003 | Moberg | 2003/0222548 A1 | 12/2003 | Richardson et al. |
| 6,558,320 B1 | 5/2003 | Causey, III et al. | 2004/0010425 A1 | 1/2004 | Wilkes et al. |
| 6,558,343 B1 | 5/2003 | Neftel | 2004/0019464 A1 | 1/2004 | Martucci et al. |
| 6,572,349 B2 | 6/2003 | Sorensen et al. | 2004/0019607 A1 | 1/2004 | Moubayed et al. |
| 6,572,604 B1 | 6/2003 | Platt et al. | 2004/0057856 A1 | 3/2004 | Saxer et al. |
| 6,632,190 B2 | 10/2003 | Simonini et al. | 2004/0064435 A1 | 4/2004 | Moubayed et al. |
| 6,641,533 B2 | 11/2003 | Causey, III et al. | 2004/0073095 A1 | 4/2004 | Causey, III et al. |
| 6,648,861 B2 | 11/2003 | Platt et al. | 2004/0078231 A1 | 4/2004 | Wilkes et al. |
| 6,670,885 B2 | 12/2003 | Kosaka | 2004/0103897 A1 | 6/2004 | Hickle et al. |
| 6,689,091 B2 | 2/2004 | Bui et al. | 2004/0107965 A1 | 6/2004 | Hickle et al. |
| 6,716,193 B1 | 4/2004 | Neftel | 2004/0116862 A1 | 6/2004 | Ray |
| 6,731,216 B2 | 5/2004 | Ho et al. | 2004/0121767 A1 | 6/2004 | Simpson et al. |
| 6,742,992 B2 | 6/2004 | Davis | 2004/0158193 A1 | 8/2004 | Bui et al. |
| 6,790,198 B1 | 9/2004 | White et al. | 2004/0167465 A1 | 8/2004 | Mihai et al. |
| 6,809,653 B1 | 10/2004 | Mann et al. | 2004/0167495 A1 | 8/2004 | Neftel |
| 6,835,049 B2 | 12/2004 | Ray | 2004/0167804 A1 | 8/2004 | Simpson et al. |
| 6,852,104 B2 | 2/2005 | Blomquist | 2004/0172222 A1 | 9/2004 | Simpson et al. |
| 6,872,200 B2 | 3/2005 | Mann et al. | 2004/0172300 A1 | 9/2004 | Mihai et al. |
| 6,889,556 B2 | 5/2005 | Steger | 2004/0172301 A1 | 9/2004 | Mihai et al. |
| 6,936,029 B2 | 8/2005 | Mann et al. | 2004/0172302 A1 | 9/2004 | Martucci et al. |
| 6,942,637 B2 | 9/2005 | Cartledge et al. | 2004/0176667 A1 | 9/2004 | Mihai et al. |
| 6,962,488 B2 | 11/2005 | Davis et al. | 2004/0176984 A1 | 9/2004 | White et al. |
| 6,966,895 B2 | 11/2005 | Tribe | 2004/0193325 A1 | 9/2004 | Bonderud et al. |
| 6,979,326 B2 | 12/2005 | Mann et al. | 2004/0225252 A1 | 11/2004 | Gillespie, Jr. et al. |
| 6,985,870 B2 | 1/2006 | Martucci et al. | 2005/0020978 A1 | 1/2005 | Vollenweider |
| 6,997,905 B2 | 2/2006 | Gillespie, Jr. et al. | 2005/0021006 A1 | 1/2005 | Tonnies |
| 6,997,920 B2 | 2/2006 | Mann et al. | 2005/0021368 A1 | 1/2005 | Burkeen et al. |
| 6,999,854 B2 | 2/2006 | Roth | 2005/0022274 A1 | 1/2005 | Campbell et al. |
| 7,001,153 B2 | 2/2006 | McDowell et al. | 2005/0029277 A1 | 2/2005 | Tachibana |
| 7,018,182 B2 | 3/2006 | O'Mahony et al. | 2005/0055242 A1 | 3/2005 | Bello et al. |
| 7,025,743 B2 | 4/2006 | Mann et al. | 2005/0055244 A1 | 3/2005 | Mullan et al. |
| 7,048,193 B2 | 5/2006 | Tsukada et al. | 2005/0065817 A1 | 3/2005 | Mihai et al. |
| 7,070,578 B2 | 7/2006 | Leukanech et al. | 2005/0069437 A1 | 3/2005 | Mittelstein et al. |
| 7,074,205 B1 | 7/2006 | Duffy et al. | 2005/0089994 A1 | 4/2005 | Neftel |
| 7,098,803 B2 | 8/2006 | Mann et al. | 2005/0095152 A1 | 5/2005 | Dale |
| 7,109,878 B2 | 9/2006 | Mann et al. | 2005/0096593 A1 | 5/2005 | Pope et al. |
| 7,117,041 B2 | 10/2006 | Engleson et al. | 2005/0101907 A1 | 5/2005 | Sondeen et al. |
| 7,141,037 B2 | 11/2006 | Butterfield et al. | 2005/0118048 A1 | 6/2005 | Traxinger |
| 7,150,735 B2 | 12/2006 | Hickle | 2005/0124929 A1 | 6/2005 | Katz et al. |
| 7,160,284 B2 | 1/2007 | Ullestad et al. | 2005/0137530 A1 | 6/2005 | Campbell et al. |
| 7,193,521 B2 | 3/2007 | Moberg et al. | 2005/0137653 A1 | 6/2005 | Friedman et al. |
| 7,195,607 B2 | 3/2007 | Westberg et al. | 2005/0139651 A1 | 6/2005 | Lim et al. |
| 7,204,823 B2 | 4/2007 | Estes et al. | 2005/0143864 A1 | 6/2005 | Blomquist |
| 7,214,038 B2 | 5/2007 | Saxer et al. | 2005/0148869 A1 | 7/2005 | Masuda |
| 7,223,079 B2 | 5/2007 | Ortega et al. | 2005/0154368 A1 | 7/2005 | Lim et al. |
| 7,236,936 B2 | 6/2007 | White et al. | 2005/0171513 A1 | 8/2005 | Mann et al. |
| 7,239,941 B2 | 7/2007 | Möri et al. | 2005/0177395 A1 | 8/2005 | Blomquist |
| 7,264,148 B2 | 9/2007 | Tachibana | 2005/0182366 A1 | 8/2005 | Vogt et al. |
| 7,311,691 B2 | 12/2007 | Cartledge et al. | 2005/0196307 A1 | 9/2005 | Limoges |
| 2001/0004444 A1 | 6/2001 | Haser et al. | 2005/0214129 A1 | 9/2005 | Greene et al. |
| 2001/0049608 A1 | 12/2001 | Hochman | 2005/0234382 A1 | 10/2005 | Tonelli et al. |
| 2002/0002326 A1 | 1/2002 | Causey, III et al. | 2005/0277873 A1 | 12/2005 | Stewart et al. |
| 2002/0016570 A1 | 2/2002 | Cartledge et al. | 2005/0277890 A1 | 12/2005 | Stewart et al. |
| 2002/0029776 A1 | 3/2002 | Blomquist | 2005/0277911 A1 | 12/2005 | Stewart et al. |
| 2002/0077852 A1 | 6/2002 | Ford et al. | 2005/0278073 A1 | 12/2005 | Roth |
| 2002/0077856 A1 | 6/2002 | Pawlikowski et al. | 2005/0283210 A1 | 12/2005 | Blischak et al. |
| 2002/0099334 A1 | 7/2002 | Hanson et al. | 2006/0001550 A1 | 1/2006 | Mann et al. |
| 2002/0104370 A1 | 8/2002 | Steger et al. | 2006/0002799 A1 | 1/2006 | Schann et al. |
| 2002/0138155 A1 | 9/2002 | Bristol | 2006/0002805 A1 | 1/2006 | Schann et al. |
| 2002/0169636 A1 | 11/2002 | Eggers et al. | 2006/0007017 A1 | 1/2006 | Mann et al. |
| 2002/0183693 A1 | 12/2002 | Peterson et al. | 2006/0009734 A1 | 1/2006 | Martin |

| | | | | | | |
|---|---|---|---|---|---|---|
| 2006/0027523 A1 | 2/2006 | Van Lintel et al. | EP | 0 332 330 | | 9/1989 |
| 2006/0058804 A1 | 3/2006 | Mollstam | EP | 0 335 385 | A2 | 10/1989 |
| 2006/0100746 A1 | 5/2006 | Leibner-Druska | EP | 0 362 822 | A2 | 4/1990 |
| 2006/0106649 A1 | 5/2006 | Eggers et al. | EP | 0 364 010 | A2 | 4/1990 |
| 2006/0116639 A1 | 6/2006 | Russell | EP | 362822 | | 4/1990 |
| 2006/0122867 A1 | 6/2006 | Eggers et al. | EP | 0 396 003 | A2 | 11/1990 |
| 2006/0129429 A1 | 6/2006 | Moubayed et al. | EP | 399119 | | 11/1990 |
| 2006/0132283 A1 | 6/2006 | Eberhart et al. | EP | 0 416 910 | | 3/1991 |
| 2006/0136271 A1 | 6/2006 | Eggers et al. | EP | 0 416 911 | | 3/1991 |
| 2006/0143051 A1 | 6/2006 | Eggers et al. | EP | 0 416 912 | | 3/1991 |
| 2006/0184121 A1 | 8/2006 | Brockman et al. | EP | 0 419 094 | | 3/1991 |
| 2006/0184123 A1 | 8/2006 | Gillespie, Jr. et al. | EP | 0 431 310 | | 6/1991 |
| 2006/0184154 A1 | 8/2006 | Moberg et al. | EP | 0 446 605 | | 9/1991 |
| 2006/0189923 A1 | 8/2006 | Neftel et al. | EP | 0 453 211 | | 10/1991 |
| 2006/0190302 A1 | 8/2006 | Eggers et al. | EP | 0 468 603 | | 1/1992 |
| 2006/0200369 A1 | 9/2006 | Batch et al. | EP | 0 495 538 | A2 | 7/1992 |
| 2006/0202859 A1 | 9/2006 | Mastrototaro et al. | EP | 0 496 436 | A2 | 7/1992 |
| 2006/0219644 A1 | 10/2006 | O'Hara, Jr. et al. | EP | 0 497 041 | | 8/1992 |
| 2006/0229551 A1 | 10/2006 | Martinez | EP | 0 499 903 | | 8/1992 |
| 2006/0243804 A1 | 11/2006 | Christoffersen et al. | EP | 0 503 670 | | 9/1992 |
| 2006/0258985 A1 | 11/2006 | Russell | EP | 0 508 556 | A1 | 10/1992 |
| 2006/0271020 A1 | 11/2006 | Huang et al. | EP | 0 524 605 | | 1/1993 |
| 2006/0287884 A1 | 12/2006 | Sandy et al. | EP | 0 544 393 | | 6/1993 |
| 2006/0287887 A1 | 12/2006 | Hutchinson et al. | EP | 0 554 716 | | 8/1993 |
| 2007/0048161 A1 | 3/2007 | Moubayed | EP | 690961 | | 1/1995 |
| 2007/0058412 A1 | 3/2007 | Wang et al. | EP | 0 648 509 | | 4/1995 |
| 2007/0060871 A1 | 3/2007 | Istoc et al. | EP | 0646382 | | 4/1995 |
| 2007/0073228 A1 | 3/2007 | Mernoe et al. | EP | 0646383 | | 4/1995 |
| 2007/0073235 A1 | 3/2007 | Estes et al. | EP | 0 681 847 | | 11/1995 |
| 2007/0073236 A1 | 3/2007 | Mernoe et al. | EP | 0 731 275 | | 9/1996 |
| 2007/0077152 A1 | 4/2007 | Knauper et al. | EP | 0 891 784 | | 1/1999 |
| 2007/0078370 A1 | 4/2007 | Shener et al. | EP | 0 893 131 | | 1/1999 |
| 2007/0078431 A1 | 4/2007 | Hudson et al. | EP | 0 893 132 | | 1/1999 |
| 2007/0083153 A1 | 4/2007 | Haar | EP | 0 898 981 | | 3/1999 |
| 2007/0083292 A1 | 4/2007 | Knauper et al. | EP | 0 899 564 | | 3/1999 |
| 2007/0088249 A1 | 4/2007 | Duffy et al. | EP | 0 919 250 | | 6/1999 |
| 2007/0088269 A1 | 4/2007 | Valego et al. | EP | 0 931 555 | | 7/1999 |
| 2007/0100316 A1 | 5/2007 | Traxinger | EP | 0 934 752 | | 8/1999 |
| 2007/0104599 A1 | 5/2007 | Michels et al. | EP | 0 985 420 | | 3/2000 |
| 2007/0106218 A1 | 5/2007 | Yodfat et al. | EP | 0 985 421 | | 3/2000 |
| 2007/0107490 A1 | 5/2007 | Artsyukhovich et al. | EP | 0 988 867 | | 3/2000 |
| 2007/0118405 A1 | 5/2007 | Campbell et al. | EP | 1 045 146 | | 10/2000 |
| 2007/0148010 A1 | 6/2007 | Michels et al. | EP | 1 101 503 | | 5/2001 |
| 2007/0156033 A1 | 7/2007 | Causey, III et al. | EP | 1 101 504 | | 5/2001 |
| 2007/0156092 A1 | 7/2007 | Estes et al. | EP | 1108891 | | 6/2001 |
| 2007/0167905 A1 | 7/2007 | Estes et al. | EP | 1225445 | | 7/2002 |
| 2007/0167912 A1 | 7/2007 | Causey et al. | EP | 1 251 276 | | 10/2002 |
| 2007/0173762 A1 | 7/2007 | Estes et al. | EP | 1 357 372 | | 10/2003 |
| 2007/0179444 A1 | 8/2007 | Causey et al. | EP | 1 391 215 | | 2/2004 |
| 2007/0212240 A1 | 9/2007 | Voyeux et al. | EP | 1 400 691 | | 3/2004 |
| 2007/0217932 A1 | 9/2007 | Voyeux et al. | EP | 1393762 | | 3/2004 |
| 2008/0015507 A1 | 1/2008 | Cartledge et al. | EP | 1 501 037 | | 1/2005 |
| 2008/0045902 A1 | 2/2008 | Estes et al. | EP | 1 532 995 | | 5/2005 |
| 2008/0045903 A1 | 2/2008 | Estes et al. | EP | 1 535 637 | | 6/2005 |
| 2008/0045904 A1 | 2/2008 | Estes et al. | EP | 1 537 886 | | 6/2005 |
| 2008/0045931 A1 | 2/2008 | Estes et al. | EP | 1 563 859 | | 8/2005 |
| | | | EP | 1576971 | | 9/2005 |
| | FOREIGN PATENT DOCUMENTS | | EP | 1 609 500 | | 12/2005 |
| | | | EP | 1 612 423 | | 1/2006 |
| DE | 41 04814 | 3/1991 | EP | 1612424 | | 1/2006 |
| DE | 4037797 | 2/1992 | EP | 1616588 | | 1/2006 |
| DE | 4307758 | 9/1994 | EP | 1 642 608 | | 4/2006 |
| DE | 19525926 | 11/1996 | EP | 1 739 585 | | 1/2007 |
| DE | 29806966 U1 | 9/1998 | EP | 1 762 263 | | 3/2007 |
| DE | 19738146 | 3/1999 | EP | 1 769 812 | | 4/2007 |
| DE | 20000965 U1 | 4/2000 | EP | 1 769 813 | | 4/2007 |
| DE | 199 16 876 | 11/2000 | EP | 1 769 815 | | 4/2007 |
| DE | 10020496 | 11/2000 | EP | 1 770 573 | | 4/2007 |
| DE | 199 60 668 | 8/2001 | EP | 1772162 | | 4/2007 |
| DE | 10022022 | 11/2001 | ES | 2238897 | | 9/2005 |
| DE | 201 01 082 | 7/2002 | FR | 2 690 622 | | 11/1993 |
| DE | 202 06 474 | 10/2003 | FR | 2792840 | | 11/2000 |
| DE | 102 44 090 | 4/2004 | GB | 1578022 | | 10/1980 |
| DE | 10359735 | 7/2005 | GB | 2109474 | | 6/1983 |
| EP | 164020 | 12/1985 | GB | 2285837 | A | 7/1995 |
| EP | 0 293 081 A1 | 11/1988 | GB | 2309801 | A | 8/1997 |
| EP | 0 293 591 A2 | 12/1988 | GB | 2312022 | | 10/1997 |
| EP | 0 036 130 A1 | 3/1989 | GB | 2312046 | | 10/1997 |
| EP | 0 319 275 A1 | 6/1989 | GB | 2312055 | | 10/1997 |
| EP | 0 327 209 A2 | 8/1989 | | | | |

| | | | | | | |
|---|---|---|---|---|---|---|
| GB | 2338752 | 12/1999 | | WO | WO 00/66203 | 11/2000 |
| GB | 2338753 | 12/1999 | | WO | WO 00/72181 | 11/2000 |
| GB | 2338754 | 12/1999 | | WO | WO 01/23277 | 4/2001 |
| GB | 2338755 | 12/1999 | | WO | WO 01/34222 | 5/2001 |
| GB | 2338756 | 12/1999 | | WO | WO 01/39816 | 6/2001 |
| GB | 2338757 | 12/1999 | | WO | WO 01/54566 | 8/2001 |
| GB | 2338758 | 12/1999 | | WO | WO 01/97113 | 12/2001 |
| GB | 2338759 | 12/1999 | | WO | WO 02/11049 | 2/2002 |
| GB | 2338760 | 12/1999 | | WO | WO 02/36044 | 5/2002 |
| GB | 2338992 | 1/2000 | | WO | WO 02/38204 | 5/2002 |
| GB | 2342188 | 4/2000 | | WO | WO 02/43573 | 6/2002 |
| GB | 2342189 | 4/2000 | | WO | WO 02/49259 | 6/2002 |
| GB | 2417052 | 2/2006 | | WO | WO 02/055137 | 7/2002 |
| JP | 9220279 | 8/1997 | | WO | WO 02/061281 | 8/2002 |
| JP | 07308379 | 4/1998 | | WO | WO 02/066101 | 8/2002 |
| JP | 2001218841 | 8/2001 | | WO | WO 02/069099 | 9/2002 |
| JP | 06205829 | 11/2001 | | WO | WO 02/081919 | 10/2002 |
| JP | 2004000498 | 1/2004 | | WO | WO03/011377 | 2/2003 |
| JP | 2004162647 | 6/2004 | | WO | WO03/024385 | 3/2003 |
| JP | 2005095577 | 4/2005 | | WO | WO 03/053503 | 7/2003 |
| JP | 2006034719 | 2/2006 | | WO | WO 03/105930 | 12/2003 |
| JP | 3124022 | 7/2006 | | WO | WO 03/105931 | 12/2003 |
| KR | 10-0516727 | 9/2005 | | WO | WO 03/105932 | 12/2003 |
| KR | 10-0553384 | 2/2006 | | WO | WO 2004/012043 | 2/2004 |
| KR | 10-0561243 | 3/2006 | | WO | WO 2004/024053 | 3/2004 |
| KR | 10-0607128 | 7/2006 | | WO | WO 2004/024214 | 3/2004 |
| KR | 10-0755528 | 8/2007 | | WO | WO 2004/033024 | 4/2004 |
| WO | WO 91/00113 | 1/1991 | | WO | WO 2004/047641 | 6/2004 |
| WO | WO 91/04759 | 4/1991 | | WO | WO 2004/087241 | 10/2004 |
| WO | WO 91/12848 | 9/1991 | | WO | WO 2004/093648 | 11/2004 |
| WO | WO 92/15349 | 9/1992 | | WO | WO 2004/095379 | 11/2004 |
| WO | WO 92/18175 | 10/1992 | | WO | WO 2004/111782 | 12/2004 |
| WO | WO 93/21978 | 11/1993 | | WO | WO 2005/032449 | 4/2005 |
| WO | WO 93/24893 | 12/1993 | | WO | WO 2005/050497 | 6/2005 |
| WO | WO 93/25816 | 12/1993 | | WO | WO 2005/056083 | 6/2005 |
| WO | WO 94/08647 | 4/1994 | | WO | WO 2005/061028 | 7/2005 |
| WO | WO 95/06817 | 3/1995 | | WO | WO 2005/062751 | 7/2005 |
| WO | WO 9517600 | 5/1995 | | WO | WO 2005/088130 | 9/2005 |
| WO | WO 95/17913 | 7/1995 | | WO | WO 2005/089263 | 9/2005 |
| WO | WO 95/24229 | 9/1995 | | WO | WO 2005/089835 | 9/2005 |
| WO | WO 96/01371 | 1/1996 | | WO | WO 2005/102417 | 11/2005 |
| WO | WO 96/03168 | 2/1996 | | WO | WO 2005/105182 | 11/2005 |
| WO | WO 96/08278 | 3/1996 | | WO | WO 2005/106251 | 11/2005 |
| WO | WO 96/08717 | 3/1996 | | WO | WO 2005/118027 | 12/2005 |
| WO | WO 96/20745 | 7/1996 | | WO | WO 2005/118054 | 12/2005 |
| WO | WO 96/20746 | 7/1996 | | WO | WO 2006/008364 | 1/2006 |
| WO | WO 96/27402 | 9/1996 | | WO | WO 2006/008376 | 1/2006 |
| WO | WO 96/28209 | 9/1996 | | WO | WO 2006/014200 | 2/2006 |
| WO | WO 96/34648 | 11/1996 | | WO | WO 2006/016122 | 2/2006 |
| WO | WO 96/36389 | 11/1996 | | WO | WO 2006/029237 | 3/2006 |
| WO | WO 97/02059 | 1/1997 | | WO | WO 2006/046242 | 5/2006 |
| WO | WO 97/07843 | 3/1997 | | WO | WO 2006/084464 | 8/2006 |
| WO | WO 97/21456 | 6/1997 | | WO | WO 2006/086701 | 8/2006 |
| WO | WO 97/32129 | 9/1997 | | WO | WO 2006/086723 | 8/2006 |
| WO | WO 97/37703 | 10/1997 | | WO | WO 2006/086735 | 8/2006 |
| WO | WO 97/37704 | 10/1997 | | WO | WO 2006/103711 | 10/2006 |
| WO | WO 97/37706 | 10/1997 | | WO | WO 2006/103712 | 10/2006 |
| WO | WO 98/13080 | 4/1998 | | WO | WO 2006/124202 | 11/2006 |
| WO | WO 98/14234 | 4/1998 | | WO | WO 2006/127905 | 11/2006 |
| WO | WO 98/20918 | 5/1998 | | WO | WO 2007/023329 | 3/2007 |
| WO | WO 98/56450 | 12/1998 | | WO | WO 2007/025268 | 3/2007 |
| WO | WO 98/56451 | 12/1998 | | WO | WO 2007/033010 | 3/2007 |
| WO | WO 98/56453 | 12/1998 | | WO | WO 2007/038059 | 4/2007 |
| WO | WO 99/10029 | 3/1999 | | WO | WO 2007/038060 | 4/2007 |
| WO | WO 99/22783 | 5/1999 | | WO | WO 2007/038091 | 4/2007 |
| WO | WO 99/47812 | 9/1999 | | WO | WO 2007/052277 | 5/2007 |
| WO | WO 99/64091 | 12/1999 | | WO | WO 2007/061368 | 5/2007 |
| WO | WO 99/64093 | 12/1999 | | WO | WO 2007/041843 | 4/2008 |
| WO | WO00/10628 | 3/2000 | | WO | WO2008/082091 | 7/2008 |
| WO | WO 00/16823 | 3/2000 | | | | |
| WO | WO 00/18449 | 4/2000 | | | | |
| WO | WO 00/21587 | 4/2000 | | | | |
| WO | WO 00/48112 | 8/2000 | | | | |
| WO | WO 00/51671 | 9/2000 | | | | |
| WO | WO 00/57941 | 10/2000 | | | | |

OTHER PUBLICATIONS

U.S. Appl. No. 11/862,302, filed Sep. 27, 2007, Voltenburg et al.
U.S. Appl. No. 11/862,360, filed Sep. 27, 2007, Voltenburg et al.

* cited by examiner

PERISTALTIC PUMP ASSEMBLY AND REGULATOR THEREFOR

BACKGROUND

The present disclosure relates generally to peristaltic pump assemblies and, more particularly, to a peristaltic pump assembly and a regulator therefor.

Peristaltic pumps are often used to deliver fluid in a very controlled manner such as, for example, the intravenous delivery of medicine to a patient. The peristaltic pump may generally include a pump body having a cassette removably attached thereto, and a tube supported by the cassette. A fluid (e.g., medicine) flows through the tube, generally by increments, as the tube is occluded against a race formed in the cassette. Occlusion of the tube may occur by a compression force applied to the tube by the rollers in response to rotational movement of a planetary system of rollers driven by a motorized drive shaft.

In some instances, small variations in the size and/or location of at least some components in the pump assembly may cause at least some variation in the compression force. This may also lead to at least some variation in the load applied to the pump motor. One way of controlling at least some of these variations is to maintain a substantially constant force applied to the tube by the rollers. This may be accomplished by coupling each roller with a spring, where the spring forces the roller against the tube via a relatively constant force.

SUMMARY

As disclosed herein, a peristaltic pump assembly includes a pump body and a cassette removably attached thereto, wherein the cassette includes a race configured to provide a compression surface for a tube supported by the cassette. A roller assembly is operatively connected to the pump body, wherein the roller assembly includes a plurality of rollers configured to apply a predetermined force to the tube, thereby compressing the tube against the race. The peristaltic pump assembly further includes a regulator disposed in the pump body and operatively connected to the cassette.

BRIEF DESCRIPTION OF THE DRAWINGS

Features and advantages of embodiment(s) of the present disclosure will become apparent by reference to the following detailed description and drawings, in which like reference numerals correspond to similar, though perhaps not identical components. Reference numerals having a previously described function may or may not be described in connection with other drawings in which they appear.

DETAILED DESCRIPTION

Embodiment(s) of the peristaltic pump assembly including the regulator as disclosed herein advantageously allow a substantially constant force to be applied on a tube, which is supported by a cassette, and by a plurality of rollers of the pump assembly. The substantially constant force applied to the tube allows the tube to be occluded by the rollers in a relatively consistent manner, thereby improving the operating performance of the pump assembly at least with regard to, e.g., the accuracy of the amount of fluid to be delivered by the pump assembly to a patient, the amount of power consumed by the pump assembly, the operating life of the cassette, the operating life of a roller mechanism employed by the pump assembly, and the operating life of a pump motor also employed by the pump assembly. The substantially constant force may also reduce the noise level of the pump assembly when the pump assembly is operating.

Other advantages of the pump assembly including the regulator include simplification of the pump assembly process, whereby adjustment(s) and/or calibration(s) of the regulator may not be necessary once the pump assembly has been assembled. Also, variations in the cassette, as well as the size and/or location of the cassette and/or other components within the pump assembly, may generally have little effect on the substantially constant force applied to the tube by the plurality of rollers.

As defined herein, the term "substantially constant force" refers to a force having a measured value remaining within about 10% of a median value. Non-limiting examples of "substantially constant forces," as referred to herein, include a substantially constant compression force and a substantially constant spring force.

Figure 1:
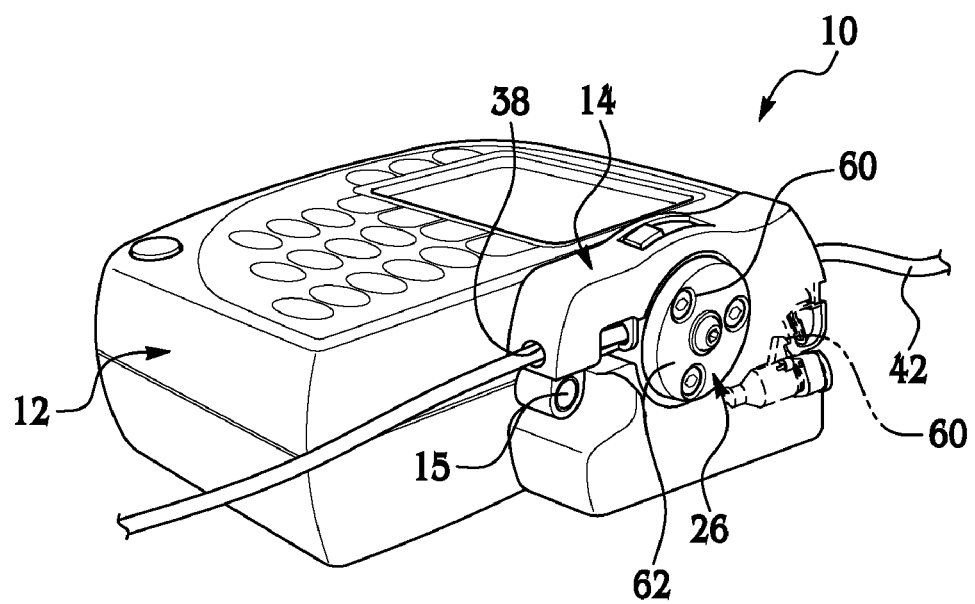
FIG. 1 is a perspective view of an embodiment of a peristaltic pump assembly including a removable cassette.
Figure 2:
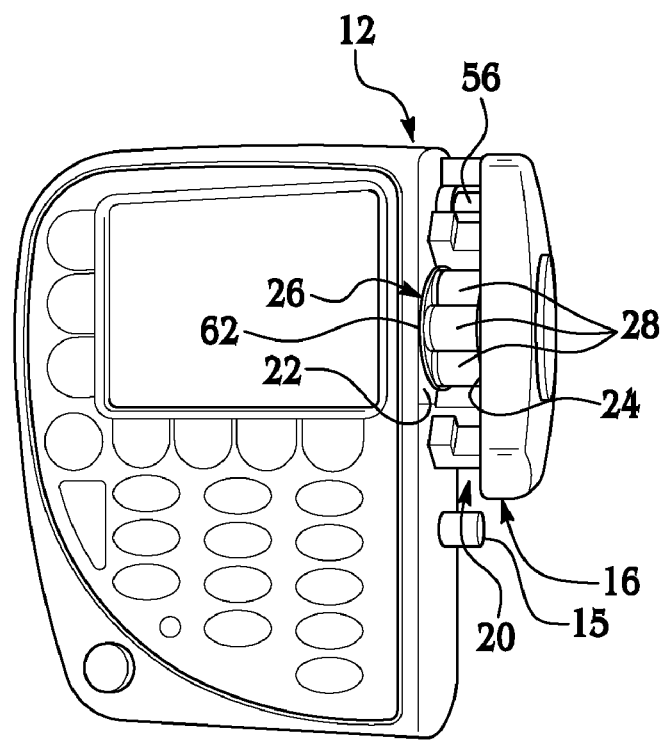
FIG. 2 is a perspective, plan view of the pump body shown in FIG. 1.

With reference to FIGS. 1 and 2, the peristaltic pump assembly 10 generally includes a pump body 12 and a cassette 14 removably attached thereto by an attachment member 15. In an illustrative example, the peristaltic pump assembly 10 will be described herein as including a mounting pin as the attachment member 15 (though it is to be understood that various alternate examples of the attachment member 15 may be used). Details of an example of a method of removably attaching the cassette 14 to the pump body 12 via the mounting pin 15 may be found in U.S. application Ser. No. 11/862,302 filed concurrently herewith, which is commonly owned by the Assignee of the present disclosure, and is incorporated herein by reference in its entirety. It is to be understood, however, that other suitable means and/or methods for removably attaching the cassette 14 to the pump body 12 may also be considered as being within the spirit and scope of the present disclosure.

The pump body 12 further includes a cassette receiving portion 16 having a partial cavity 20 defined by a floor (not shown) and two opposing walls 22, 24. A roller assembly 26 (e.g., a roller mechanism) is housed within the cavity 20 and operatively connected to the pump body 12. Roller assembly 26 includes a plurality of satellite rollers 28 arranged in a planetary configuration. The rollers 28 rotate as an assembly, as well as individually, in response to rotational forces imparted thereto by a motorized drive shaft (not shown). The motorized drive shaft may be operated by a pump motor (not shown), which are both operatively connected to the pump body 12.

Figure 3:
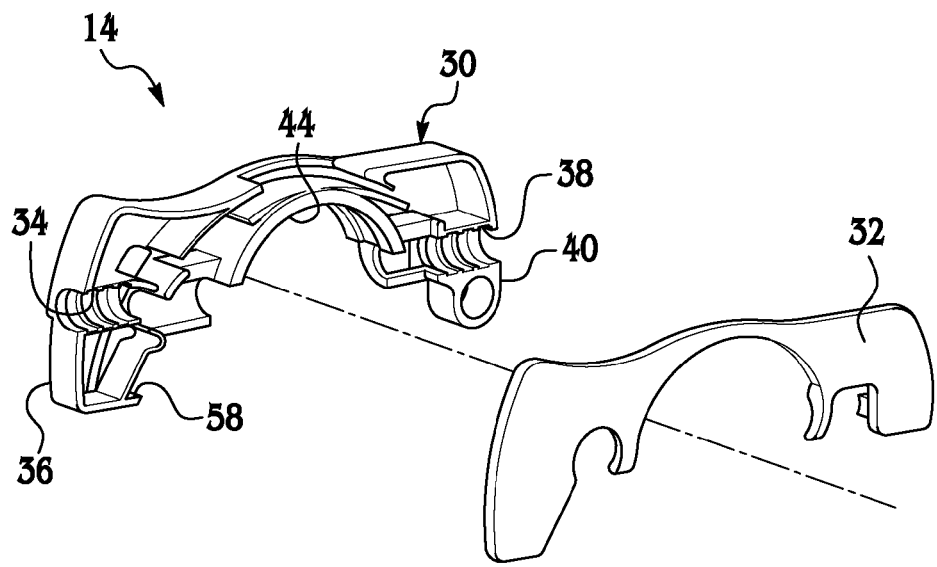
FIG. 3 is an enlarged, exploded, perspective view of the removable cassette shown in FIG. 1.

An exploded view of the cassette 14 is generally depicted in FIG. 3, where the cassette 14 includes a cassette body 30 and a cover 32 disposed thereon. The cassette 14 may be disposable, as desired. The cassette body 30 includes an inlet 34 formed in an end 36 thereof and an outlet 38 formed in another end 40 thereof. The inlet 34 and outlet 38 are configured to receive first and second ends of a tube 42 (shown in FIG. 1), thereby supporting the tube 42 in the cassette 14.

In a non-limiting example, the tube 42, which is also disposable, may be classified as substantially flexible so that the tube may be compressed and/or occluded by the rollers 28, as will be described further below. In an embodiment, the tube 42 is made of a polymeric material. Non-limiting examples of suitable polymeric materials include silicones, AUTOPRENE (an opaque thermoplastic rubber with high wear resistance derived from SANTOPRENE, commercially available from Advanced Elastomer Systems, a subsidiary of ExxonMobil Chemical located in Houston, Tex.), VITON (a black fluoroelastomer with resistance to concentrated acids, solvents, ozone, radiation and temperatures up to 200° C. with good chemical compatibility, commercially available from DuPont Performance Elastomers located in Wilmington, Del.), TYGON (good chemical resistance with a clear finish, commercially available from Saint-Gobain Performance Plastics Corporation located in Akron, Ohio), PROTHANE II (a transparent, blue, polyester, polyurethane tubing with good chemical resistance, commercially available from Randolph Austin Company located in Manchaca, Tex.), and/or the like, and/or combinations thereof. The inner diameter of the tube 42 may be selected based on the desirable flow rates and the desirable viscosities of the fluid that will flow therethrough.

The cassette 14 further includes a race 44 formed therein and configured to provide a compression surface for the tube 42. It is to be understood that during operation of the pump, the rollers 28 apply a compression force against the tube 42 in response to rotational movement of the rollers 28. The compression force compresses the tube 42 against the race 44 to thereby substantially occlude the tube 42. This compression force is a predetermined force controlled by a regulator 46 of the pump assembly 10. As such, in response to the rotational movement of the rollers, portions of the flexible tube 42 that are in contact with the rollers 28 compress or are otherwise occluded against a wall of the cassette 14. As a result, fluid is temporarily retained in the tube 42 between the occluded points. In this manner, fluid is urged through the tube 42 via peristaltic wave action. Details of an example of a suitable cassette 14 may be found in U.S. application Ser. No. 11/862,360, filed concurrently herewith, which is commonly owned by the Assignee of the present disclosure, and is incorporated herein by reference in its entirety.

Figure 4:
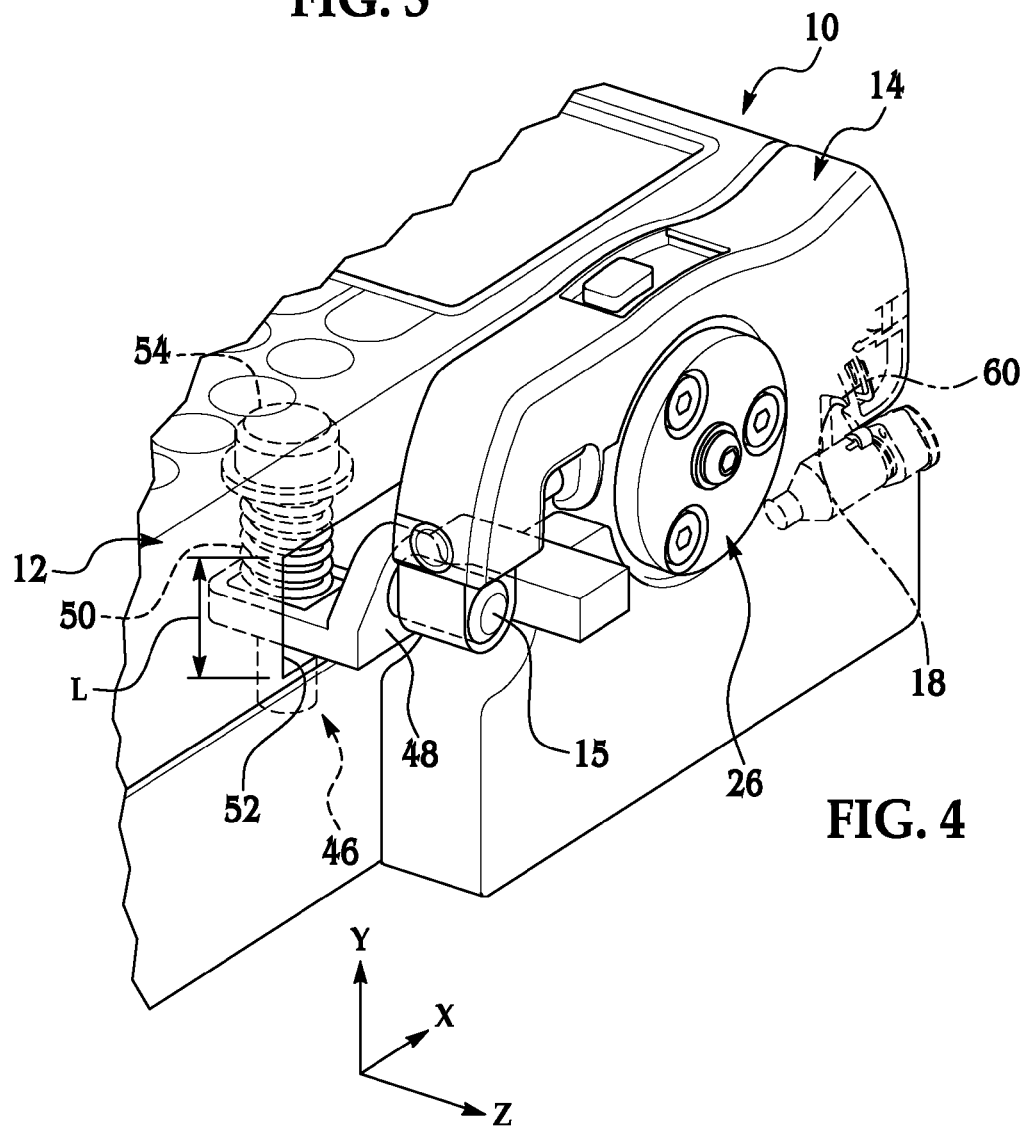
FIG. 4 is a cutaway, perspective view of the pump assembly depicting an embodiment of a regulator disposed therein.

As depicted in FIG. 4, the regulator 46 is disposed in the pump body 12 and is operatively connected to the cassette 14. It is to be understood, however, that the regulator 46 may otherwise be disposed in the peristaltic pump assembly 10, e.g. adjacent to the pump body 12 and/or as part of the pumping mechanism assembly. In an embodiment, the regulator 46 includes a slide member 48 having the mounting pin 15 connected thereto. The slide member 48 may be any suitable support member capable of moving along a substantially linear path of length L. In an embodiment, and as shown in FIG. 4, a window 52 is formed in the pump body 12. At least a portion of the slide member 48 extends through the window 52. The window 52 is configured to allow the slide member 48 (including the mounting pin 15 connected thereto) to linearly slide or otherwise move a distance along a length L in response to changes/variations in the pump assembly 10 or components thereof (e.g., variations in the wall thickness of the tube 42 at the compression area of the race 44, wear of the rollers 28, thermal length variations of components, manufacturing variations, etc.).

Movement of the slide member 48 (e.g., in the window 52) may be restricted by the regulator 46 via a spring 50 also provided therewith and operatively connected to the slide member 48. The spring 50 may be operatively situated such that the spring 50 compresses along substantially the same linear direction as the slide member 48. In an embodiment, the spring 50 may be selected from those having a spring constant ranging from about 3 $lb_f$/in (0.525 N/mm) to about 5 $lb_f$/in (0.875 N/mm). Non-limiting examples of suitable springs include helical springs, clock springs, torsion springs, compression springs, extension springs, leaf springs, elastomeric bodies, and/or the like, and/or combinations thereof.

In an embodiment, a predetermined pre-load may be applied to the spring 50 using a pre-loading member 54 operatively connected thereto. As shown in FIG. 4, the pre-loading member 54 may be a shoulder bolt extending through the spring 50 and through a bore (not shown) formed in the slide member 48. It is to be understood that other devices may suitably be used as the pre-loading member 54, non-limiting examples of which include screws, pegs, pins, shafts, and/or the like, and/or combinations thereof. In a non-limiting example, the predetermined pre-load applied to the spring 50 ranges from about 1.5 $lb_f$ (7 N) to about 3 $lb_f$ (14 N).

The regulator 46 is generally configured to regulate and/or control the compression force applied to the tube 42 by the rollers 28 so that the compression force is a substantially constant force. To accomplish this, the regulator 46 restricts the amount of the compression force applied to the tube 42 within a predetermined boundary or range. The predetermined boundary or range may be determined, e.g., based on the spring constant of the spring 50 and the distance that the slide member 48 travels in order to compress the spring 50. Restricting the amount of the compression force may be accomplished by allowing the mounting pin 15 (which is connected to the slide member 48) to move in response to changes and/or variations in the peristaltic pump assembly 10. In a non-limiting example, such changes and/or variations include variations in the individual components of, or the assembly 10 as a whole (as mentioned above), e.g., when the assembly 10 is infusing a fluid to a patient.

In an embodiment, before the cassette 14 is mounted to the pump body 12, the slide member 48 is slightly pre-loaded (e.g., a pre-load of about 2 $lb_f$ to about 2.5 $lb_f$) via compression of the spring 50. Upon mounting the cassette 14, the slide member 48 moves in the y-direction from its pre-load position, and the spring 50 compresses slightly further beyond the pre-load force. The tube 42 is substantially occluded under the force applied by the spring 50. During operation of the roller mechanism, as the rollers 28 rotate, slight variations and/or changes in the size of the tube 42, various components of the cassette 14, the rollers 28, and/or the like are controlled by the slide member 48 by moving the slide member 48, against the spring 50, in the y-direction along the substantially linear path of length L. It is to be understood that movement of the slide member 48 is relatively small in order to sufficiently control the changes in the pump assembly 10 components, etc., and to maintain a substantially constant compression force applied to the tube 42 by the rollers 28. In a non-limiting example, the slide member 48 moves a length L ranging from about 0.25 mm to about 0.5 mm.

Although the pump assembly 10 has been described including the regulator 46 operatively connected to the mounting pin 15, it is to be understood that the regulator 46 may otherwise be operatively connected to a pump body retaining feature 56 (shown in FIG. 2) disposed or otherwise formed in the pump body 12. In an embodiment, the pump body retaining feature 56 is configured to matingly engage a cassette retaining feature 58 (shown in FIG. 3) formed on the cassette body 30, thereby securing the cassette 14 to the pump body 12 when assembled therewith.

Also disclosed herein is a method of regulating the predetermined force applied to the tube 42 by a plurality of rollers 28 in the peristaltic pump assembly 10, thereby compressing the tube 42. The method is accomplished by providing pump assembly 10 including the regulator 46, and regulating the predetermined force applied to the tube 42.

It is to be understood that the term "connect/connected" or the like is broadly defined herein to encompass a variety of divergent connecting arrangements and assembly techniques. These arrangements and techniques include, but are not limited to (1) the direct connection between one component and another component with no intervening components therebetween; and (2) the connection of one component and another component with one or more components therebetween, provided that the one component being "connected to" the other component is somehow operatively coupled to the other component (notwithstanding the presence of one or more additional components therebetween).

While several embodiments have been described in detail, it will be apparent to those skilled in the art that the disclosed embodiments may be modified. Therefore, the foregoing description is to be considered exemplary rather than limiting.

What is claimed is:

1. A peristaltic pump assembly, comprising:
   a pump body;
   a cassette removably attached to the pump body, wherein the cassette includes a race configured to provide a compression surface for a tube supported by the cassette;
   a roller assembly operatively connected to the pump body to rotate about an axis of rotation, wherein the roller assembly includes a plurality of rollers configured to apply a force to the tube, thereby compressing the tube against the race; and
   a regulator disposed in the pump body and operatively connected to the cassette, wherein the regulator is configured to regulate the force applied to the tube;
   wherein the regulator includes:
      an L-shaped slide member having a first leg and a second leg perpendicular to the first leg, wherein the first leg and the second leg are non-rotatable relative to each other;
      a pre-loading member, wherein the second leg of the slide member is mounted on the pre-loading member to permit the slide member to move as a unit in a linear direction relative to the pre-loading member;
      a mounting pin carried by the first leg for rotatably mounting the cassette to the slide member, the mounting pin defining an axis of rotation of the cassette, wherein the mounting pin moves with the slide member in the linear direction;
      a spring operatively connected to the second leg to apply a force in a direction orthogonal to the axis of rotation defined by the mounting pin.

2. The peristaltic pump assembly as defined in claim 1 wherein the pre-loading member engages the spring and extends through an opening in the second leg, wherein the pre-loading member is configured to apply an adjustable pre-load to the spring.

3. The peristaltic pump assembly as defined in claim 2 wherein the adjustable preload ranges from about 1.5 lbf to about 3 lbf.

4. The peristaltic pump assembly as defined in claim 2 wherein the pre-loading member is selected from shoulder bolts, screws, pegs, pins, shafts, or combinations thereof.

5. The peristaltic pump assembly as defined in claim 1 wherein, when the mounting pin moves with the slide member, the regulator regulates the force applied to the tube.

6. The peristaltic pump assembly as defined in claim 2 wherein the force applied to the tube, the preload to the spring, or combinations thereof are constant.

7. The peristaltic pump assembly as defined in claim 1 wherein the spring is selected from helical springs, clock springs, torsion springs, compression springs, extension springs, leaf springs, elastomeric bodies, or combinations thereof.

8. The peristaltic pump assembly as defined in claim 1 wherein the spring has a spring constant ranging from about 3 lbf/in to about 5 lbf/in.

9. A regulator for a peristaltic pump, the regulator comprising:
   an L-shaped slide member having a first leg and a second leg perpendicular to the first leg, wherein the first leg and the second leg are non-rotatable relative to each other;
   a pre-loading member, wherein the second leg of the slide member is mounted on the pre-loading member to permit the slide member to move as a unit in a linear direction relative to the pre-loading member;
   a mounting pin carried by the first leg defining an axis of rotation, wherein the mounting pin moves with the slide member in the linear direction;
   a spring operatively connected to the second leg to apply a force in a direction orthogonal to the axis of rotation defined by the mounting pin;
   wherein the regulator regulates a force applied to a tube by a plurality of rollers of a roller assembly of the peristaltic pump.

10. The regulator as defined in claim 9 wherein when the mounting pin moves, the regulator regulates the force applied to the plurality of rollers.

11. A method of regulating a force applied to a tube by a plurality of rollers of a roller assembly in a peristaltic pump, thereby compressing the tube, the method comprising:
   regulating the force applied to the tube using a regulator disposed in a pump body of the peristaltic pump and operatively connected to a cassette, the cassette being removably attached to the pump body, the cassette including a race configured to provide a compression surface for the tube;
   wherein the regulator includes:
      an L-shaped slide member having a first leg and a second leg perpendicular to the first leg, wherein the first leg and the second leg are non-rotatable relative to each other;
      a pre-loading member, wherein the second leg of the slide member is mounted on the pre-loading member to permit the slide member to move as a unit in a linear direction relative to the pre-loading member;
      a mounting pin carried by the first leg defining an axis of rotation, wherein the mounting pin moves with the slide member in the linear direction;
      a spring operatively connected to the second leg to apply a force in a direction orthogonal to the axis of rotation defined by the mounting pin.

12. The method as defined in claim 11 wherein regulating the force applied to the tube is accomplished by moving the mounting pin.

13. The method as defined in claim 12 wherein moving the mounting pin is accomplished by:
   compressing the spring upon mounting the cassette to the pump body; and
   allowing the slide member including the mounting pin to move along a linear path.

* * * * *